United States Patent [19]

Cheng et al.

[11] Patent Number: 5,266,319
[45] Date of Patent: Nov. 30, 1993

[54] TANNIN DERIVATIVES AND THEIR USE FOR TREATMENT OF HYPERTENSION

[75] Inventors: Juei-Tang Cheng; Feng-Lin Hsu, both of Taipei, Taiwan

[73] Assignee: National Science Council, Taipei, Taiwan

[21] Appl. No.: 853,059

[22] Filed: Mar. 18, 1992

[51] Int. Cl.$^5$ .................... A61K 35/78; A61K 31/70
[52] U.S. Cl. ........................ 424/195; 514/23; 514/25
[58] Field of Search ............. 424/195.1; 514/783, 514/23, 25

[56] References Cited

U.S. PATENT DOCUMENTS 3,879,547  4/1975  Thuillier .................. 424/195

OTHER PUBLICATIONS

Journal of Natural Products, 52:1 pp. 210-211 (Jan.-Feb. 1989).
Heterocycles, 15:2 (1981).
Phytochemistry 19, pp. 547-551 (1980).
Planta Medica (1989).
Planta Medica 55 (1989).
Yaugaku Zasshi 99 (1979).
Chem. Pharm. Bull. 32 (9) 3755-3758 (1984). 32 (1984).
Phytochemistry 21L5, pp. 1049-1062 (1982).
Steinmetz F., Codex Vegetabilis, Amsterdam 1957 #1099.
Yoshida, Tannins and Related Polyphenols . . . , Bio Abstracts 86 (1) 116949 1988.
Hatano, Tannins of Cornaceous Plants, Bio Abstr. 88 (11) 122805 1989.
Nonaka, Tannins and Related Compounds, Bio Abstr. 90 (3)31411 1990.
Hatano; Gallotannins having a 1,5-anhydro-D-. . . Bio Abstracts 90(9) 102701 1990.
Okuda, Japan Kokai, 78 31,687 Chem. Abstracts 89:30759j No. 3, 1978.
Umishio, Transdermal Tannin Preparations, Chem Abstracts 116 (3) 28185b Jan. 20, 1992.

*Primary Examiner*—Michael G. Witshyn
*Assistant Examiner*—Ralph G. Gitomer
*Attorney, Agent, or Firm*—Fish & Richardson

[57] ABSTRACT

Disclosed is a treatment of hypertension with an effective amount of tannins extracted from *Sapium sebiferum* leaves, the tannins are 6-O-galloyl-D-glucose, corilagin, geraniin and 1,2,3,4,6-penta-O-galloyl-β-D-glucose.

6 Claims, No Drawings

TANNIN DERIVATIVES AND THEIR USE FOR TREATMENT OF HYPERTENSION

BACKGROUND OF THE INVENTION

The present invention relates to the use of tannins extracted from *Sapium sebiferum* for treating hypertension, wherein the tannins are 6-O-galloyl-D-glucose, corilagin, geraniin and 1,2,3,4,6-penta-O-galloyl-β-D-glucose.

Hypertension is a prevalent disease in developed countries. There are some effective drug therapies used to decrease arterial pressure and control the morbidity of hypertension. However, some side effects have been observed during clinical applications of these drugs when administered to patients for a long period. As a result, it is necessary to find some new antihypertensive drugs so that a clinical physician has more choices of drugs for treatment without greatly inducing side effects.

In the conventional medical treatment of hypertension, some agents are prepared from natural plants or animals drugs. However, as hypertensive these drugs are not accepted by the western medicine since, besides the effective compound, they contain some other ineffective compounds. Therefore, the effective components should be purified the so that their actual treating effect the can be experimented and verified.

SUMMARY OF THE INVENTION

It is an object of the present invention to provide a pharmaceutical composition which comprises an effective amount of tannins extracted from the leaves of *Sapium sebiferum* for the treatment of hypertension.

For achieving the above-mentioned object, the extracts from *Sapium sebiferum* are dissolved in a saline solution, then they are administered to a hypertensive rat through intraperitoneal injection. As a result, it was found that the extracts can reduce the blood pressure at a concentration of 10 mg/kg, thereby verifying that the extracts contain potent components which produce vasorelaxation. Therefore, four compounds were further extracted and purified from *Sapium sebiferum* leaves and the compounds were found to be tannins. These four potent compounds are 6-O-galloyl-D-glucose, corilagin, geraniin and 1,2,3,4,6-penta-O-galloyl-β-D-glucose.

DETAILED DESCRIPTION OF THE INVENTION

Fresh leaves of *Sapium sebiferum* are dipped in a 80% acetone solution under room temperature. After 24 hours, the extract is concentrated under reduced pressure, and it is dissolved in a saline solution, then it is injected intraperitoneally to a hypertensive rat. As a result, the blood pressure is depressed by $30.5 \pm 12.9$ mmHg (N=12) at a concentration of 10 mg/kg. Therefore the extract which is rich in tannin may contain an active compound for the treatment of hypertension.

After the removal of acetone, the residual solution of the extract is filtered to remove the precipitate. The filtrate is separated and purified by column chromatography using polydextran gel (e.g. Sephadex) and a suitable solvent, and the recovery rate is quite high. Furthermore, high porous polystyrene gel (e.g. Diaion) and reverse-phase packing (e.g. Fuji-gel ODS, Bondapak $C_{18}$/porasil B) are also used to separate the analogous compounds. Consequently, four tannin compounds are obtained, they are 6-O-galloyl-D-glucose (compound I), corilagin (compound II), geraniin (compound III) and 1,2,3,4,6-penta-O-galloyl-β-D-glucose (compound IV).

The structural formula of the tannins are showed as below:

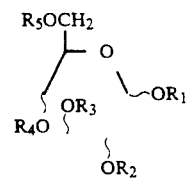

where R1, R2, R3, R4 and R5 represent

|  | R1 | R2 | R4 | R3 | R5 |
|---|---|---|---|---|---|
| Compound I | H | H | H | H | G |
| Compound II | G | H | H | (HHDP) | |
| Compound III | G | (DHHDP) | | (HHDP) | |
| Compound IV | G | G | G | G | G |

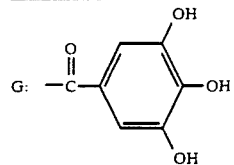

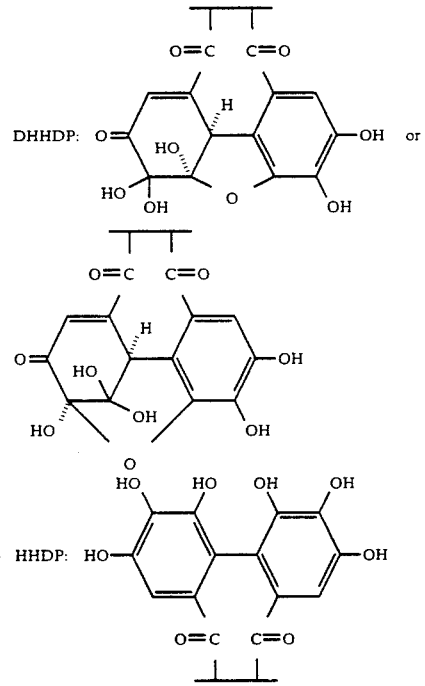

wherein
HHDP bonds to $R_3$ and $R_5$; and
DHHDP bonds to $R_2$ and $R_4$.

The effect of the tannins of the present invention have been studied to evaluate the use of these compounds in the treatment of hypertension. The results verified that the four tannins possess the ability to decrease blood pressure.

Therefore, the active compounds of the present invention can be admixed with pharmaceutically acceptable diluent and carrier, so that they can be administered orally in solid dosage forms, such as capsules, tablets, and powders, or in liquid dosage forms, such as elixirs, syrups, and suspensions, or can be administered parenterally in sterile liquid dosage forms.

The following examples serve to demonstrate the pharmacological activities of the claimed compounds. These are not intended as limiting since numerous modifications and varieties thereof will be apparent to those skilled in the art.

EXAMPLE 1

The preparation of the compounds from *Sapium sebiferum* leaves 6 kg of fresh *Sapium sebiferum* leaves were dipped in an 80% acetone solution for over 24 hours at room temperature. Then, the extract was concentrated under reduced pressure at 45° C. to remove the acetone, and the residual aqueous solution was filtered. The filtrate was chromatographed over a Sephadex LH-20 column and $H_2O$ -MeOH was used as an eluant. The first 20% MeOH eluate was discarded, and the 30-50% MeOH eluate (Fr.2) the 80-100% MeOH eluate were collected. The 60-70 % MeOH eluate did not contain active components, and. Fr. 2 was treated by Diaion column ($H_2O$ -MeOH) and the 30-40% MeOH eluate was collected, then subjected to a MCI column ($H_2O$ -MeOH), wherein the 20-30 % MeOH eluate was collected. At last, the eluate was purified using a Bondapak $C_{18}$ column ($H_2O$ -MeOH) and the 20-25% eluate was collected. 220 mg of 6-O-galloyl-D-glucose was obtained after the eluate was concentrated under reduced pressure. On the other hand, Fr. 4 was treated by MCI column ($H_2O$ -MeOH) and the 20-30 % eluate was collected, then the eluate was purified by Sephadex column (EtOH), Fuji-ODS column (15-20 % MeOH), Sephadex column (EtOH and 80% MeOH) respectively, and 80 mg of corilagin was obtained.

In the elution by MCI column chromatography for Fr. 4, geraniin (30 g) was obtained from the 50-60 % MeOH eluate, and 1,2,3,4,6-penta-O-galloyl-$\beta$-D-glucose (210 mg) was obtained from the 30-40 % MeOH eluate in Fuji-ODS column chromatography.

The characteristics and spectral analysis of the compounds obtained are stated as follows:

1. 6-O-galloyl-D-glucose (Compound I)
   white solid powder ($H_2O$ ), $C_{13}H_{16}O_{10}$.
   $[\alpha]$: +25.3° (C=0.5, $H_2O$ )
   mp: 137°-139° C.
   IR $\gamma_{max}^{kBr}$ cm$^{-1}$: 3600-3000 (OH), 1700 (C=O), 1610 (C=C)
   $^1$H-NMR (acetone-$d_6$+$D_2O$): $\delta$ 3.47-5.18 (7H, m, sugar H), 7.15 (2H, s, galloyl-H)
   $^{13}$C-NMR (acetone-$d_6$+$D_2O$): $\delta$ 64.5(C-6$\alpha$, $\beta$), 70.3(C-4$\alpha$), 71.0(C-4$\beta$), 71.2(C-2$\alpha$), 73.1(C-5$\beta$), 74.2(C-3$\alpha$), 74.7(C-2$\beta$), 75.6(C-5$\beta$), 77.3(C-3$\alpha$), 93.3(C-1$\alpha$), 97.7(C-1$\beta$), 109.7 (galloyl C-2, C-6 , 121.2(galloyl C-1), 138.8(galloyl C-4), 145.9(galloyl C-3,C-5), 167.2(—COO—).

Hydrolysis of 6-O-galloyl-D-glucose with tannase at 37° C. furnished gallic acid and glucose, which were identified by thin-layer co-chromatography with authentic samples.

2. corilagin (Compound II)
   white needles ($H_2O$ ), $C_{27}H_{22}O_{18}$
   $[\beta]$: −136.7° (C=1.0, EtOH)
   mp: 218°-220° C.
   $^1$H-NMR (acetone-$d_6$) $\delta$ 4.06(1H,brs,H-2), 4.11(1H,m,H-6), 4.46(1H,brs,H-4), 4.52(1H,t,J=10.8 Hz,H-5), 4.82(1H,brs,H-3), 4.95(1H,t,J=10.8 Hz,H-6), 6.38(1H,d,J=2 Hz,H-1), 6.71, 6.82(each 1H,s,HHDP-H), 7.12(2H,s,galloyl-H).
   $^{13}$C-NMR (acetone-$d^6$): $\delta$ 61.7(C-4), 64.8(C-6), 68.3(C-2 , 70.2(C-3), 74.9(C-5), 94.0(C-1), 107.5, 109.8(HHDP C-3'), 110.3(galloyl C-2, C-6), 115.3, 116.3(HHDP C-1, C-1'), 119.8(galloyl C-1), 124.6, 124.9(HHDP C-2, C-2'), 136.1, 136.8(HHDP C-5, C-5'), 139.2(galloyl C-4), 144.3(HHDP C-4, C-4', C-6'), 145.3(galloyl C-3, C-5), 165.5, 167.0, 168.5 (ester carbon).

Hydrolysis of corilagin with 0.1N HCl was performed for 1 hr and the solution was chromatographed over Sephadex LH-20 using ($H_2O$ -MeOH, 10:0−3:7) to give ellagic acid ($^1$H-NMR in DMSO-$d_6$: $\delta$ 7.45, 2H, s), gallic acid ($^1$H-NMR in acetone-$d_6$: $\delta$ 7.14, 2H, s) and glucose (Rf=0.45, cellulose plate, n-BuOH:pyridine:$H_2O$=6:4:3, under aniline hydrogen phthalate spray as brown spot)

3. Geraniin (Compound III)
   a tan amorphous powder ($H_2O$ ), $C_{41}H_{28}O_{27}$
   mp>300° C.
   $[\alpha]$: −141.0° (C=1.1, MeOH)
   $^1$H-NMR (acetone-$d_6$): $\delta$ 4.28(1H,m,H-5 , 4.67-5.00(2H,m, h-3,6), 517(1H,s,H-1'), 5.40-5.60(3H,m,H-2,4,6), 6.53(1H,s,H-3'), 6.56(1H,s,H-1'), 6.67(1H,s,HHDP-H), 7.13(1H,s,HHDP-H), 7.20(3H,brs,galloyl-H,H-3'').
   $^{13}$C-NMR (acetone): $\delta$ 62.3(glc. C-3), 63.8(glc. C-6), 66.8(glc. C-4), 70.4(glc. C-2), 73.1(glc. C-5), 91.8(glc. C-1), 110.9(galloyl C-2,6), 120.2(galloyl C-1), 139.9(galloyl C-4), 146.0(galloyl C-3,5), 108.8(HHDP C-3), 110.6(HHDP C-3'), 115.8(HHDP C-1'), 117.2(HHDP C-1), 124.6(HHDP C-2), 125.6(HHDP C-2'), 136.6(HHDP C-5), 137.9(HHDP C-5'), 145.0 (HHDP C-6), 145.1(HHDP C-6'), 145.5(HHDP C-4),145.8(HHDP C-4'), 113.5(DHHDP C-3'), 115.3(DHHDP C-1'), 119.4(DHHDP C-139.0(DHHDP C-5'), 143.4(DHHDP C-6'), 144.6(DHHDP C-4'), 46.2(DHHDP C-1), 96.3(DHHDP C-5), 108.0(DHHDP C-6), 128.6(DHHDP C-3), 154.5(DHHDP C-2), 191.8(DHHDP C-4), 164.8, 165.4, 165.6, 166.1, 168.4 (ester carbon).

Hydrolysis of geraniin in boiling water, gallic acid ellagic acid and corilagin were produced, which were identified by thin-layer co-chromatography with authentic samples.

4. 1,2,3,4,6-penta-O-galloyl-$\beta$-D-glucose (Compound IV)
   a tan amorphous powder, $C_{41}H_{32}O_{26}$
   $[\beta]$: +17.6° (C=1.0, acetone)
   $^1$H-NMR (acetone-$d_6$): $\delta$ 4.30-4.68(3H,m,H-5,6), 5.61(1H, t,J=9 Hz,H-2), 5.66(1H,dd,J=9,8 Hz,H-4), 6.03(1H,t,J=9 Hz,H-3), 6.34(1H,d,J=8Hz,H-1), 6.96, 7.00, 7.05, 7.11, 7.16 (each 2H, s,galloyl-H).
   $^{13}$H-NMR (acetone-$d_6$): $\delta$ 62.8(C-6), 69.2(C-4), 71.7(C-2), 73.3(C-3), 73.9(C-5), 93.3(C-1), 164.9(galloyl C-1), 165.5(galloyl C-4), 165.6(galloyl C-2), 165.8(galloyl C-3), 166.3(galloyl C-6).

Hydrolysis of 1,2,3,4,6-penta-O-galloyl-$\beta$-D-glucose with tannase at 37° C. furnished gallic acid and glucose.

EXAMPLE 2

The effect on the blood pressure of spontaneously hypertensive rats (SHR) and normal rats (WKY)

The tannins obtained in the example 1 were injected into various rats respectively at different concentrations. As a result, the four compounds were found to be effective in the depression of the tail arterial blood pressure of spontaneously hypertensive rats (SHR) and also slightly effective on the blood pressure of normal rats (WKY). The results are summarized in table 1.

TABLE 1

| Depression of blood pressure (mmHg) | SHR | WKY |
|---|---|---|
| 6-O-galloyl-D-glucose | | |
| 1 mg/kg | 17.28 ± 7.08 | 5.81 ± 5.07 |
| 5 mg/kg | 24.12 ± 9.93 | 5.21 ± 3.48 |
| Corilagin | | |
| 1 mg/kg | 17.85 ± 3.38 | 3.85 ± 2.64 |
| 5 mg/kg | 26.57 ± 7.92 | 10.85 ± 4.89 |
| Geraniin | | |
| 1 mg/kg | 19.28 ± 5.49 | 3.57 ± 4.72 |
| 5 mg/kg | 25.85 ± 4.18 | 13.28 ± 6.67 |
| 1,2,3,4,6-penta-O-galloyl-D-glucose | | |
| 1 mg/kg | 13.28 ± 6.22 | 2.62 ± 2.33 |
| 5 mg/kg | 29.57 ± 13.38 | 5.74 ± 2.41 |

The data (Means±S.D.) in table 1 represents the value of the depression range of blood pressure (N=11). In comparison to conventional antihypertensive drugs, guanethidine can depress the blood pressure of hypertensive rats in a range of 28.8±7.95 mmHg (N=8) with a injection concentration of 1 mg/kg, prazosin in a range of 31.4±7.17 mmHg (N=8) and nifedipine in a range of 10.8±2.78 mmHg (N=8) at the same concentration.

As shown in table 1, the present compounds are comparable to conventional drugs, e.g. prazosin (a $\alpha_1$-adrenoceptor blocker), nifedipine (a calcium-channel blocker) and guanethidine (a drug for relaxing adrenercic tension).

EXAMPLE 3

The effect on the concentration of norepinephrine in blood

Four tannins were injected to the veins of various rats respectively at different concentrations. After ten minutes, the blood of the rats were sampled to determine the concentration of norepinephrine in their blood. Obviously, these compounds can reduce the concentration of norepinephrine, i.e., they can inhibit the secretion of norepinephrine and relax the adrenergic tension, and therefore the blood pressure can be reduced. The results are showed in table 2.

TABLE 2

| | Plasma NE (pmoles/ml) |
|---|---|
| Control | 3.55 ± 0.31 |
| 6-O-galloyl-D-glucose | |
| 1 mg/kg | 2.14 ± 0.09 |
| 5 mg/kg | 1.76 ± 0.22 |
| Corilagin | |
| 0.5 mg/kg | 2.19 ± 0.22 |
| 1 mg/kg | 1.55 ± 0.19 |
| Geraniin | |
| 0.5 mg/kg | 2.66 ± 0.19 |
| 1 mg/kg | 2.17 ± 0.09 |
| 1,2,3,4,6-penta-O-galloyl-D-glucose | |
| 1 mg/kg | 1.94 ± 0.19 |
| 5 mg/kg | 1.23 ± 0.21 |

Means ± S.D are presented (N = 6). NE: norepinephrine

EXAMPLE 4

The effect on the contraction of rat blood vessel

Norepinephrine and octopamine were injected into various anesthetized normal rats respectively, so that a contraction of rat blood vessels was induced and the blood pressure increased. However, the blood pressure of the rats was reduced by the compounds of the present invention significantly (see table 3). Therefore, the tannins are potent in inhibiting the contraction of blood vessels and the effect of the tannins on the wall of blood vessel is also significant.

TABLE 3

| Inhibition (%) | Octopamine ($8 \times 10^{-4}$ g/kg) | Norepinephrine ($10^{-6}$ g/kg) |
|---|---|---|
| 6-O-galloyl-D-glucose | 65.3 ± 11.3 | 64.1 ± 15.1 |
| corilagin | 65.5 ± 27.5 | 83.4 ± 7.3 |
| geraniin | 74.8 ± 13.5 | 87.1 ± 6.5 |
| 1,2,3,4,6-penta-O-galloyl-D-glucose | 72.1 ± 14.8 | 70.6 ± 10.7 |

Dose: 1 mg/kg, i.v., Means ± S.D. are presented (n = 8)

Furthermore, the lethal dosages ($LD_{50}$) for the rats were determined. The $LD_{50}$ of corilagin and geraniin were greater than 100 mg/kg, and the $LD_{50}$ of 6-O-galloyl-D-glucose and 1,2,3,4,6-penta-O-galloyl-D-glucose were greater than 50 mg/kg. Therefore, these four tannins can be used as a safe and effective hypertensive drugs.

What is claimed is:

1. A pharmaceutical composition for treating hypertension, which comprises an effective amount of 6-O-galloyl-D-glucose, which has a formula of:

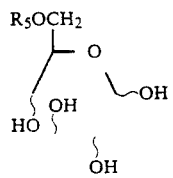

wherein $R_5$ represents

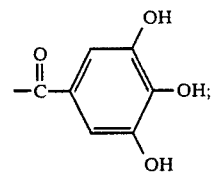

and pharmaceutically acceptable diluent and carrier.

2. A method for treating hypertension, comprising administering a pharmaceutical composition as claimed in claim 1 to a human.

3. A method for treating hypertension, comprising administering parenterally a pharmaceutical composition as claimed in claim 1 to a mammal.

4. A pharmaceutical composition for treating hypertension, which comprises an effective amount of corilagin, which has a formula of:

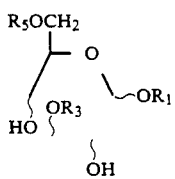

wherein $R_1$ represents

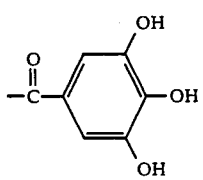

; and $R_3$ and $R_5$ together are

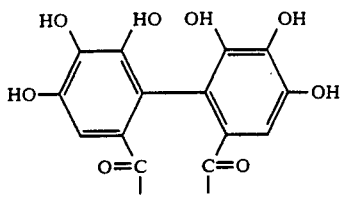

; and pharmaceutically acceptable diluent and carrier.

5. A method for treating hypertension, comprising administering a pharmaceutical composition as claimed in claim 4 to a human.

6. A method for treating hypertension, comprising administering parenterally a pharmaceutical composition as claimed in claim 4 to a mammal.

* * * * *